United States Patent [19]

Förster et al.

[11] Patent Number: 4,622,415

[45] Date of Patent: Nov. 11, 1986

[54] OPTICALLY ACTIVE PHENOXYPROPIONIC ACID DERIVATIVES

[75] Inventors: Heinz Förster; Bernd Gallenkamp, both of Wuppertal; Uwe Priesnitz, Solingen; Hans-Jochem Riebel, Wuppertal; Ludwig Eue, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 761,243

[22] Filed: Jul. 31, 1985

Related U.S. Application Data

[63] Continuation of Ser. No. 614,575, May 25, 1984.

[30] Foreign Application Priority Data

May 27, 1983 [DE] Fed. Rep. of Germany ....... 3319290

[51] Int. Cl.⁴ .............................................. C07C 69/76
[52] U.S. Cl. ..................................... 560/62; 562/472; 260/544 D; 548/373; 556/437; 71/108; 71/109
[58] Field of Search .......................... 560/62; 562/472; 260/544 D; 548/373; 556/437; 71/108, 109

[56] References Cited

FOREIGN PATENT DOCUMENTS

EP34120 8/1981 European Pat. Off. .............. 560/21

Primary Examiner—Paul J. Killos
Attorney, Agent, or Firm—Sprung Horn Kramer & Woods

[57] ABSTRACT

There is disclosed an R enantiomer of phenoxypropionic acid compound of the formula

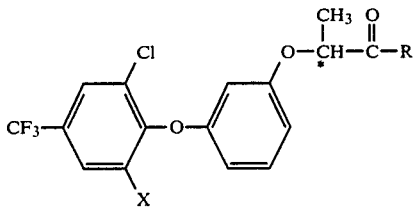

in which X represents hydrogen or halogen, and R represents hydroxyl, alkoxy, halogen or the radical of the formula

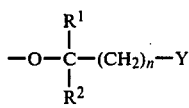

wherein $R^1$ and $R^2$ independently of one another represent hydrogen or methyl, n represents 0, 1 or 2 and Y represents trimethylsilyl, or optionally substituted azolyl bonded via nitrogen, or represents alkoxy, alkoxycarbonyl or the radical of the formula

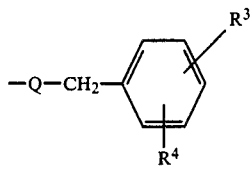

wherein Q represents oxygen, sulphur, SO or SO₂ and $R^3$ and $R^4$ independently of one another represent hydrogen, halogen, alkyl having 1 to 4 carbon atoms, alkoxy having 1 to 4 carbon atoms, alkylthio having 1 to 4 carbon atoms, nitro, cyano or alkoxycarbonyl having 1 to 4 carbon atoms in the alkoxy group; compositions containing herbicidally effective amounts of such R enantiomers and the use of such R enantiomers as herbicides.

20 Claims, No Drawings

OPTICALLY ACTIVE PHENOXYPROPIONIC ACID DERIVATIVES

This is a continuation of application Ser. No. 614,575, filed May 25, 1984.

The invention relates to new R enantiomers(*) of phenoxypropionic acid derivatives, several processes for their preparation and their use as herbicides.

(*)In the present case, R enantiomers are understood as meaning those optically active compounds which have the R configuration at the asymmetrically substituted carbon atom of the propionic acid unit.

It is known that a large number of phenoxypropionic acid derivatives possess herbicidal properties (see DE-OS (German Published Specification) No. 2,805,981). Thus, for example, the racemate of ethyl 2-[3-(2,6-dichloro-4-trifluoromethyl-phenoxy)-phenoxy]-propionate can be employed for combating weeds. The action of this substance is good, but, when it is used in small amounts, some weeds are not always completely combated.

New R enantiomers of phenoxypropionic acid derivatives of the formula

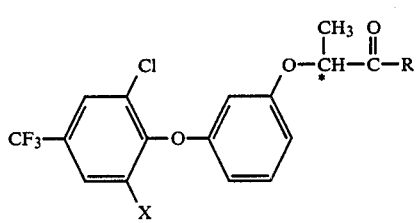

in which

X represents hydrogen or halogen, and
R represents hydroxyl, alkoxy, halogen or the radical of the formula

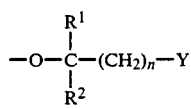

wherein $R^1$ and $R^2$ independently of one another represent hydrogen or methyl,
n represents 0, 1 or 2 and
Y represents trimethylsilyl, or optionally substituted azolyl bonded via nitrogen, or represents alkoxy, alkoxycarbonyl or the radical of the formula

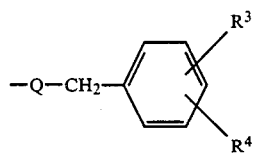

in which

Q represents oxygen, sulphur, SO or $SO_2$ and
$R^3$ and $R^4$ independently of one another represent hydrogen, halogen, alkyl having 1 to 4 carbon atoms, alkoxy having 1 to 4 carbon atoms, alkylthio having 1 to 4 carbon atoms, nitro, cyano or alkoxycarbonyl having 1 to 4 carbon atoms in the alkoxy group, have now been found.

Furthermore, it has been found that the new R enantiomers of phenoxypropionic acid derivatives of the formula (I) are obtained if (a) diphenyl ether derivatives of the formula

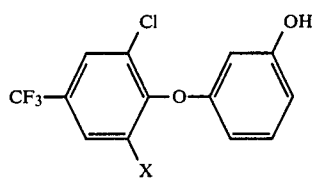

in which

X has the meaning given above, are reacted with S enantiomers of the propionic acid derivative of the formula

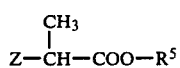

in which

Z represents tosylate or mesylate and
$R^5$ represents alkyl or the radical of the formula

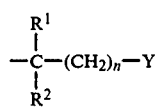

wherein $R^1$, $R^2$ and n have the meaning given above and
Y represents trimethylsilyl, optionally substituted azolyl which is bonded via nitrogen, alkoxy, alkoxycarbonyl or the radical of the formula

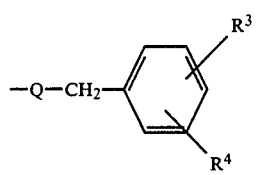

wherein $R^3$, $R^4$ and Q have the meaning given above, if appropriate in the presence of an acid acceptor and, if appropriate, in the presence of a diluent, and, if required, the product is then hydrolyzed in the presence of a diluent, and, if desired, resulting R enantiomers of phenoxypropionic acid derivatives of the formula

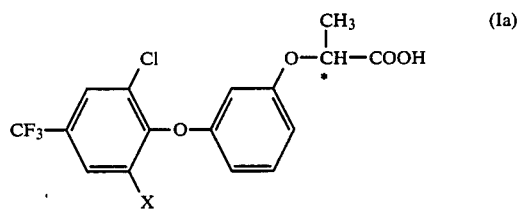

in which X has the meaning given above, are converted to the corresponding acid-halides by halogenation, or (b) R enantiomers of phenoxypropionic acid derivatives of the formula

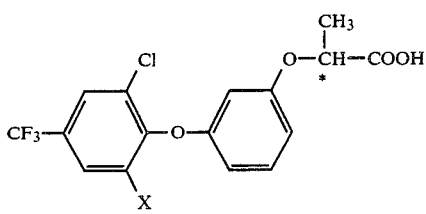

in which X has the meaning given above, are reacted
(α) with silyl chlorides of the formula

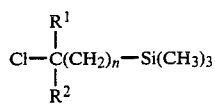

in which R¹, R² and n have the meaning given above, or
(β) with compounds of the formula

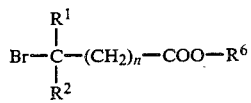

in which
R¹, R² and n have the meaning given above and
R⁶ represents alkyl, in each, if appropriate, case in the presence of an acid-binding agent and, if appropriate, in the presence of a diluent, or (c) R enantiomers of phenoxypropionic acid-chlorides of the formula

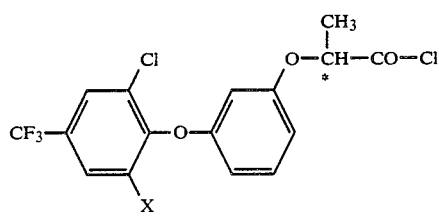

in which X has the meaning given above, are reacted with hydroxy compounds of the formula

R⁷—OH  (VI)

in which R⁷ represents alkyl or the radical of the formula

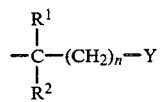

wherein R¹, R², Y and n have the meaning given above, if appropriate in the presence of an acid acceptor and, if appropriate, in the presence of a diluent.

Finally, it has been found that the new R enantiomers of phenoxypropionic acid derivatives of the formula (I) are distinguished by outstanding herbicidal activity.

Surprisingly, the R enantiomers of the phenoxypropionic acid derivatives according to the invention, of the formula (I), possess substantially better herbicidal properties than the racemates of these substances. Thus, for example, the R enantiomer of ethyl 2-[3-(2,6-dichloro-4-trifluoromethyl-phenoxy)-phenoxy]-propionate has a superior herbicidal activity to the corresponding racemate, which is known from the prior art to be a highly effective herbicide.

Formula (I) gives a general definition of the R enantiomers of phenoxypropionic acid derivatives according to the invention. In this formula, in which the asymmetrically substituted carbon atom is marked with an (*), X preferably represents hydrogen or chlorine. R preferably represents hydroxyl, chlorine, bromine, alkoxy having 1 to 4 carbon atoms or the radical of the formula

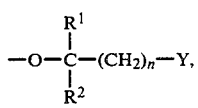

wherein

R¹ and R² independently of one another represent hydrogen or methyl, n represents 0, 1 or 2 and Y preferably represents trimethylsilyl, or a pyrazolyl, imidazolyl, 1,2,4-triazolyl, 1,2,3-triazolyl or 1,3,4-triazolyl radical bonded via a ring nitrogen atom, it being possible for each of these azolyl radicals to be monosubstituted or polysubstituted by identical or different substituents from amongst fluorine, chlorine, bromine, iodine, alkyl having 1 to 4 carbon atoms, alkoxy having 1 to 4 carbon atoms and phenyl.

Furthermore, Y preferably represents alkoxy having 1 to 4 carbon atoms, alkoxycarbonyl having 1 to 4 carbon atoms in the alkoxy part or the radical of the formula

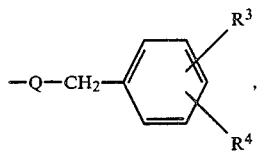

wherein

Q represents oxygen, sulphur, SO or SO₂ and

R³ and R⁴ independently of one another preferably represent hydrogen, fluorine, chlorine, bromine, iodine, alkyl having 1 or 2 carbon atoms, alkoxy having 1 or 2 carbon atoms, alkylthio having 1 or 2 carbon atoms, nitro, cyano or alkoxycarbonyl having 1 or 2 carbon atoms in the alkoxy group.

Those R enantiomers of the formula (I) in which R¹ represents methyl and R² represent hydrogen contain a second centre of asymmetry in the ester unit. The substances in question can therefore occur in the following forms:

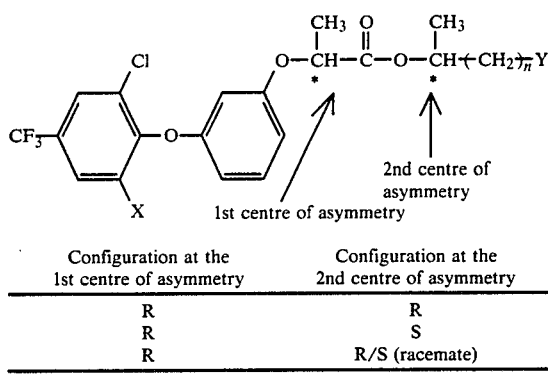

| Configuration at the 1st centre of asymmetry | Configuration at the 2nd centre of asymmetry |
|---|---|
| R | R |
| R | S |
| R | R/S (racemate) |

The present invention embraces those compounds which have the R or the S configuration at the second centre of asymmetry, as well as the corresponding racemates.

If 2,6-dichloro-4-trifluoromethyl-3'-hydroxydiphenyl ether and the S enantiomer of (ethoxycarbonyl)methyl 2-tosyloxy-propionate are used as starting materials, the course of process (a) according to the invention can be represented by the following equation:

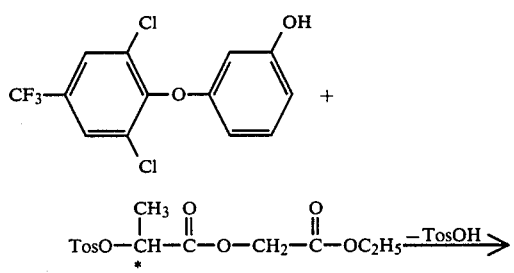

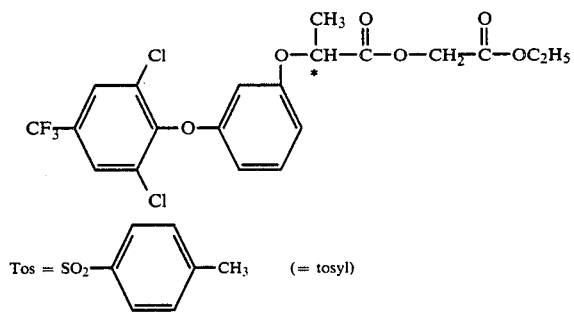

If the R enantiomer of 2-[3-(2-chloro-4-trifluoromethyl-phenoxy)-phenoxy]-propionic acid and chloromethyltrimethyl-silane are used as starting materials, the course of process (b, variant α) according to the invention can be represented by the following equation:

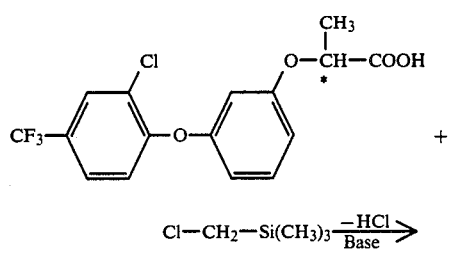

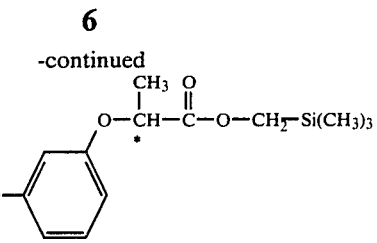

If the R enantiomer of 2-[3-(2,6-dichloro-4-trifluoromethyl-phenoxy)-phenoxy]-propionic acid and ethyl bromoacetate are used as starting materials, the course of process (b, variant β) according to the invention can be represented by the following equation:

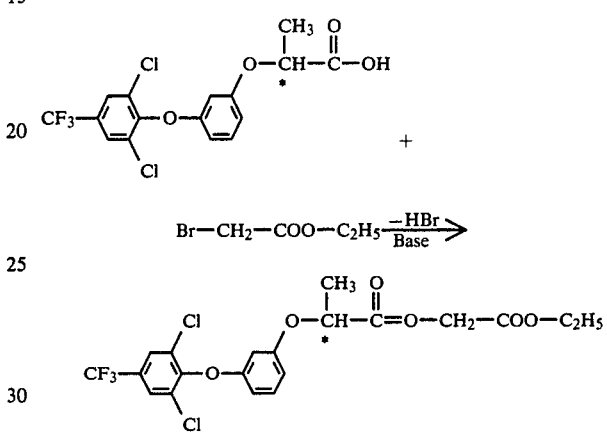

If the R enantiomer of 2-[3-(2,6-dichloro-4-trifluoromethyl-phenoxy)-phenoxy]-propionic acid-chloride and 2-(pyrazol-1-yl)-ethanol are used as starting materials, the course of process (c) according to the invention can be represented by the following equation:

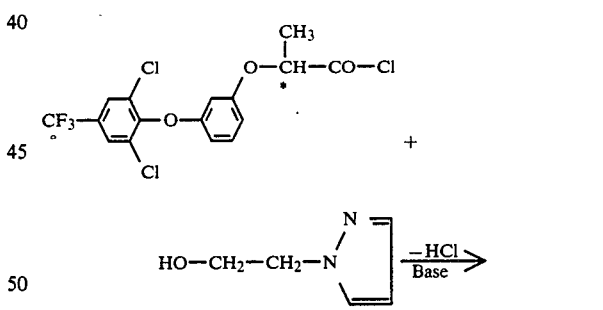

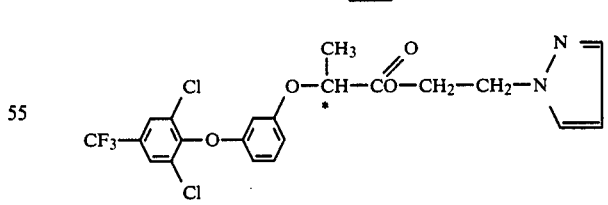

Formula (II) gives a definition of the diphenyl ether derivatives required as starting materials in carrying out process (a) according to the invention. In this formula, X preferably represents hydrogen or chlorine.

The diphenyl ether derivatives of the formula (II) are known (see DE-OS (German Published Specification) No. 2,805,981).

Formula (III) gives a definition of the S enantiomers of the propionic acid derivatives furthermore required as starting materials in process (a) according to the invention. In this formula, Z represents tosylate

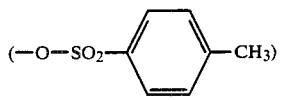

or mesylate (—O—SO$_2$—CH$_3$). R$^5$ preferably represents alkyl having 1 to 4 carbon atoms or the radical of the formula

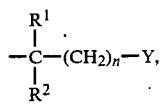

wherein
R$^1$ and R$^2$ independently of one another represent hydrogen or methyl,
n represents 0, 1 or 2 and
Y preferably represents trimethylsilyl or a pyrazolyl, imidazolyl, 1,2,4-triazolyl, 1,2,3-triazolyl or 1,3,4-triazolyl radical bonded via a ring nitrogen atom, it being possible for each of these azolyl radicals to be monosubstituted or polysubstituted by identical or different substituents from amongst fluorine, chlorine, bromine, iodine, alkyl having 1 to 4 carbon atoms, alkoxy having 1 to 4 carbon atoms and phenyl. Furthermore, Y represents alkoxy having 1 to 4 carbon atoms, alkoxycarbonyl having 1 to 4 carbon atoms in the alkyl part or the radical of the formula

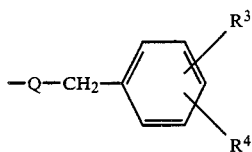

wherein
Q represents oxygen, sulphur, SO or SO$_2$, and
R$^3$ and R$^4$ independently of one another preferably represent hydrogen, fluorine, chlorine, bromine, iodine, alkyl having 1 or 2 carbon atoms, alkoxy having 1 or 2 carbon atoms, alkylthio having 1 or 2 carbon atoms, nitro, cyano or alkoxycarbonyl having 1 or 2 carbon atoms in the alkoxy group.

Those substances of the formula (III) in which R$^5$ represents the radical

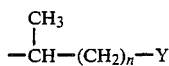

contain, in the ester moiety, a second centre of asymmetry which can have the R or S configuration. In the corresponding racemates, the asymmetrically substituted carbon atom in the ester moiety makes no contribution to the optical activity of the S enantiomers of the propionic acid derivatives of the formula (III).

The S enantiomers of the propionic acid derivatives of the formula (III) are known, or can be prepared in a simple manner by customary methods. Thus, the S enantiomers of the propionic acid derivatives of the formula (III) are obtained by reacting S enantiomers of propionyl chlorides of the formula

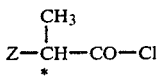

in which Z has the meaning given above, with hydroxy compounds of the formula

in which R$^5$ has the meaning given above, if appropriate in the presence of an acid acceptor and, if appropriate, in the presence of a diluent.

The S enantiomers of propionyl chlorides of the formula (VII) which are required as starting materials in the preparation of the S enantiomers of the propionic acid derivatives of the formula (III) are known, or can be prepared by known methods. The hydroxy compounds of the formula (VIII) which are also required as reactants for the reaction for the synthesis of the S enantiomers of the propionic acid derivatives of the formula (III) are likewise known, or can be prepared in a simple manner by known methods.

In this process for the preparation of the S enantiomers of the propionic acid derivatives of the formula (III), the reaction conditions correspond to those of process (a) according to the invention (see below).

S enantiomers of the phenoxypropionic acid derivatives of the formula (III) have to be employed in process (a) according to the invention because, in the course of the reaction, a Walden inversion takes place at the asymmetrically substituted carbon atom of the propionic acid unit.

All acid-binding agents which can be customarily used for reactions of this type can be employed as acid acceptors in process (a) according to the invention. Preferred compounds are alkali metal hydroxides, alkaline earth metal hydroxides and oxides, such as, for example, sodium hydroxide and potassium hydroxide, calcium hydroxide and calcium oxide, alkali metal carbonates and alcoholates, such as sodium carbonate and potassium carbonate, sodium methylate, potassium methylate, sodium ethylate and potassium ethylate, and also aliphatic, aromatic or heterocyclic amines, for example triethylamine, trimethylamine, dimethylaniline, dimethylbenzyl-amine, 1,5-diazabicyclo-[4.3.0]-non-5-ene (DBN), 1,8-diazabicyclo[5.4.0]-undec-7-ene (DBU) and pyridine.

In carrying out process (a) according to the invention, suitable diluents are all inert organic solvents. Compounds which can be preferably used are aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide and dimethylacetamide and N-methyl-pyrrolidone, as well as dimethyl sulphoxide, tetramethylene sulphone and hexamethylphosphoric acid triamide.

In the reaction according to process (a) according to the invention, the reaction temperatures can be varied within a relatively wide range. In general, the reaction is carried out at temperatures between −20° C. and +160° C., preferably between 0° C. and +140° C.

Process (a) according to the invention is carried out in general under atmospheric pressure. However, it is also possible to employ elevated or reduced pressure.

To carry out process (a) according to the invention, the starting materials of the formulae (II) and (III) are employed in general in approximately equimolar amounts. However, it is also possible to use a relatively large excess of one of the two components used in each case. The reactions are carried out in general in a suitable diluent in the presence of an acid acceptor, and the reaction mixture is stirred for several hours at the particular temperature required. Working-up is carried out in each case by customary processes.

If it is intended to prepare a compound of the formula (I) in which R represents hydroxyl, advantageously an ester (R=alkoxy) prepared by process (a) according to the invention is hydrolysed by customary methods. Aqueous alkali metal hydroxide solutions, such as, for example, sodium hydroxide solution or potassium hydroxide solution, are preferably used as hydrolysis reagents.

The ester hydrolysis is carried out in general in the presence of a diluent. Preferred diluents are aromatic hydrocarbons, such as toluene or xylene, alcohols, such as methanol or ethanol, ethers, such as dioxane, and nitriles, such as acetonitrile, as well as mixtures of organic solvents and water.

In carrying out the ester hydrolysis, the temperatures can be varied within a relatively wide range. In general, the reaction is carried out at temperatures between 0° C. and 160° C., preferably between 20° C. and 140° C.

In carrying out the ester hydrolysis, in general the ester of the formula (I) is treated with an equivalent amount or with an excess of base in the presence of a diluent at the particular temperature desired. Working-up is carried out by customary methods. In general, the procedure is as follows: the reaction mixture is evaporated down by stripping off the solvent under reduced pressure, the remaining residue is taken up in water, the solution is acidified with a mineral acid, such as, for example, hydrochloric acid, and the acid of the formula (I) which separates out is isolated.

If the preparation of a compound of the formula (I) intended, in which R represents halogen, the procedure is advantageously as follows: an acid (R=hydroxyl) prepared by process (a) according to the invention is reacted with the halogenating agent, such as, for example, thionyl chloride, thionyl bromide or phosphorus tribromide, if appropriate in the presence of a catalyst, such as, for example, dimethylformamide, in the presence of an inert diluent, such as, for example, methylene chloride or 1,2-dichloroethane, at temperatures between 10° and 100° C. Working-up is carried out by customary methods.

Formula (Ia) gives a definition of the R enantiomers of the phenoxypropionic acid derivatives required as starting materials in process (b) according to the invention, In this formula, X represents hydrogen or chlorine.

The compounds of the formula (Ia) can be prepared from esters of the formula (I) according to the invention, in which R represents alkoxy, in the manner described above, by hydrolysis.

Formula (IV) gives a definition of the silyl chloride furthermore required as starting materials in process (b, variant α) according to the invention. In this formula, $R^1$, $R^2$ and n preferably have those meanings which have already been mentioned in connection with the description of the substances according to the invention, of the formula (I), as being preferred for these radicals and for the index n.

The silyl chlorides of the formula (IV) are known, or can be prepared in a simple manner by known methods.

Formula (V) gives a definition of the compounds furthermore required as starting materials in process (b, variant β) according to the invention. In this formula, $R^1$, $R^2$ and n preferably have those meanings which have already been mentioned in connection with the description of the substances according to the invention, of the formula (I), as being preferred for these radicals and for the index n. $R^6$ preferably represents alkyl having 1 to 4 carbon atoms.

Those substances of the formula (V) in which $R^1$ represents methyl and $R^2$ represents hydrogen can occur either as racemates or as R or S enantiomers. If the R enantiomers of these compounds of the formula (V) are used in process (b, variant β) according to the invention, those substances according to the invention which have the S configuration at the second centre of asymmetry are formed, because a Walden inversion takes place in the course of the reaction. Correspondingly, the S enantiomers of the compounds of the formula (V) give those substances according to the invention which possess the R configuration at the second centre of asymmetry. When racemates of the compounds of the formula (V) are used, the substances according to the invention which are obtained are those in which the asymmetrically substituted carbon atom in the ester moiety makes no contribution to the optical activity of the end products.

The compounds of the formula (V) are known, or can be prepared in a simple manner by known methods.

In carrying out process (b) according to the invention, both variant α and variant β are preferably carried out in the presence of an acid acceptor and of a diluent. Preferred acid-binding agents and diluents are all those substances which have already been mentioned in this connection in the case of process (a) according to the invention as being preferred.

In process (b) according to the invention, both in variant α and in variant β, the reaction temperatures can also be varied within a relatively wide range. In general, the reaction is carried out in each case at temperatures between −20° C. and +160° C., preferably between 0° C. and +140° C.

Process (b), both in variant α and in variant β, is carried out in general under atmospheric pressure. However, it is also possible to employ elevated or reduced pressure.

To carry out process (b, variants α and β) according to the invention, the starting materials of the formulae (Ia) and (IV) or (V) are employed in general in approximately equimolar amounts.

However, it is also possible to use a relatively large excess of one of the two components employed in each case. The reactions are carried out in general in a suitable diluent in the presence of an acid acceptor, and the reaction mixture is stirred for several hours at the particular temperature required. Working-up is carried out in each case by customary processes.

Formula (Ib) gives a definition of the R enantiomers of the phenoxypropionic acid-chlorides required as starting materials in process (c) according to the invention. In this formula, X represents hydrogen or chlorine. The compounds of the formula (Ib) can be prepred by process (a) according to the invention (see above).

Formula (VI) gives a definition of the hydroxy compounds furthermore required as starting materials in process (c) according to the invention. In this formula, $R^7$ preferably represents alkyl having 1 to 4 carbon atoms or the radical of the formula

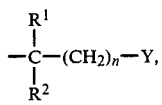

wherein $R^1$ and $R^2$ independently of one another represent hydrogen or methyl, n represents 0, 1 or 2 and Y preferably represents trimethylsilyl or a pyrazolyl, imidazolyl, 1,2,4-triazolyl, 1,2,3-triazolyl or 1,3,4-triazolyl radical bonded via a ring nitrogen atom, it being possible for each of these azolyl radicals to be monosubstituted or polysubstituted by identical or different substituents from amongst fluorine, chlorine, bromine, iodine, alkyl having 1 to 4 carbon atoms, alkoxy having 1 to 4 carbon atoms and phenyl.

Furthermore, Y preferably represents alkoxy having 1 to 4 carbon atoms, alkoxycarbonyl having 1 to 4 carbon atoms in the alkoxy part or the radical of the formula

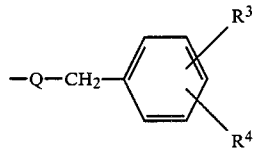

wherein

Q represents oxygen, sulphur, SO or $SO_2$ and $R^3$ and $R^4$ independently of one another preferably represent hydrogen, fluorine, chlorine, bromine, iodine, alkyl having 1 or 2 carbon atoms, alkoxy having 1 or 2 carbon atoms, alkylthio having 1 or 2 carbon atoms, nitro, cyano or alkoxycarbonyl having 1 or 2 carbon atoms in the alkoxy group.

The hydroxy compounds of the formula (VI) are known, or can be prepared in a simple manner by known processes.

In carrying out process (c) according to the invention, the reaction is carried out in general in the presence of a diluent and in the presence of an acid-binding agent. Preferred diluents and acid acceptors are all those substances which have already been mentioned in this connection in the case of process (a) according to the invention as being preferred.

In process (c) according to the invention, the reaction temperatures can also be varied within a relatively wide range. In general, the reaction is carried out at temperatures between −20° C. and +160° C., preferably between 0° C. and +140° C.

Process (c) according to the invention is carried out in general under atmospheric pressure. However, it is also possible to employ elevated or reduced pressure.

To carry out process (c) according to the invention, the starting materials of the formulae (Ib) and (VI) are employed in general in approximately equimolar amounts. However, it is also possible to use one of the two components in a relatively large excess. If a relatively large excess of the hydroxy compound is employed, it is not necessary to add a diluent in some cases. Working-up is carried out by customary methods.

The active compounds according to the invention can be used as defoliants, desiccants and agents for destroying broad-leaved plants, and especially as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylenefattyacid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixing being possible.

Suitable herbicides for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethyl-urea for combating weeds in cereals; 4-amino-3-methyl-6-phenyl-1,2,4-triazin-5(4H)-one for combating weeds in sugar beet, and 4-amino-6-(1,1-dimethylethyl)-3-methylthio-1,2,4-triazin-5(4H)-one for combating weeds in soya beans. Surprisingly, some mixtures also exhibit a synergistic effect.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil area, preferably between 0.05 and 10 kg per ha.

The preparation and the use of the active compounds according to the invention are evident from the examples below.

PREPARATION EXAMPLES

EXAMPLE 1

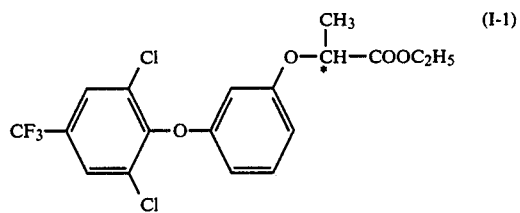

A mixture of 96.9 g (0.3 mol) of 2,6-dichloro-4-trifluoromethyl-3'-hydroxy-diphenyl ether, 81.7 g (0.3 mol) of the S enantiomer of ethyl 2-tosyloxy-propionate and 82.8 g (0.6 mol) of potassium carbonate in 800 ml of acetonitrile were heated under reflux for 3 hours. Thereafter, working-up was carried out by filtering the reaction mixture under suction, evaporating down the filtrate, dissolving the remaining residue in methylene chloride, washing the resulting solution once with water, drying it and then evaporating it down under reduced pressure. The remaining residue was freed from residues of volatile constituents by gentle heating in a high vacuum. In this manner, the R enantiomer of ethyl 2-[3-(2,6-dichloro-4-trifluoromethyl-phenoxy)-phenoxy]-propionate was obtained in a yield of 97% of theory.

Angle of rotation: $[\alpha]_D^{24} = +1.5°$ (1 molar solution in chloroform; cell length 10 cm).

EXAMPLE 2

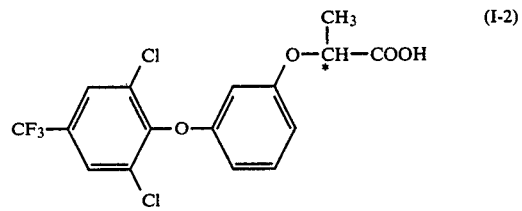

A solution of 51.4 g (0.124 mol) of the R enantiomer of ethyl 2-[3-(2,6-dichloro-4-trifluoromethyl-phenoxy)-phenoxy]-propionate in 95 ml of ethanol was added dropwise to a stirred solution of 5.9 g (0.148 mol) of sodium hydroxide in 145 ml of water at 0° C. During this procedure, the reaction mixture foamed to such an extent that, after ⅔ of the ester solution had been added, a further 10 ml of ethanol had first to be introduced into the reaction mixture before the remainder of the ester solution could be added. Stirring was continued for a further 16 hours, while cooling with ice, and working-up was then carried out by acidifying the mixture with hydrochloric acid, extracting the resulting mixture three times with methylene chloride, drying the extracts and evaporating them down. The remaining residue was boiled with petroleum ether, and the hot mixture was filtered under suction. In this manner, 47.6 g (97.1% of theory) of the R enantiomer of 2-[3-(2,6-dichloro-4-trifluoromethyl-phenoxy)-phenoxy]-propionic acid were obtained in the form of a solid substance of melting point 120° C.

Angle of rotation: $[\alpha]_D^{24} = -1.9°$ (1 molar solution in chloroform; cell length 10 cm).

EXAMPLE 3

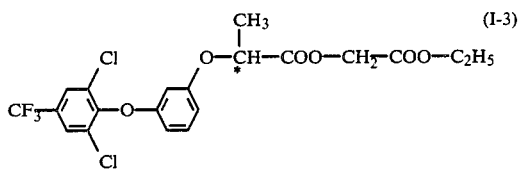

A mixture of 41.0 g (0.104 mol) of the R enantiomer of 2-[3-(2,6-dichloro-4-trifluoromethyl-phenoxy)-phenoxy]-propionic acid, 15.8 g (0.114 mol) of potassium carbonate and 17.4 g (0.104 mol) of ethyl bromoacetate in 104 ml of acetonitrile was heated under reflux for 1 hour. Thereafter, working-up was carried out by filtering the reaction mixture under suction, evaporating down the filtrate, taking up the remaining residue in methylene chloride, and washing this solution once with water, drying it and then evaporating it down. The remaining residue was freed from residues of volatile constituents by gentle heating in a high vacuum. In this manner, 34.9 g (70% of theory) of the R enantiomer of (ethoxycarbonyl)-methyl 2-[3-(2,6-dichloro-4-trifluoromethylphenoxy)-phenoxy]-propionate were obtained in the form of a liquid having a refractive index $n_D^{20} = 1.5190$.

Angle of rotation: $[\alpha]_D^{24} = +4.68°$ (1 molar solution in chloroform; cell length 10 cm).

EXAMPLE 4

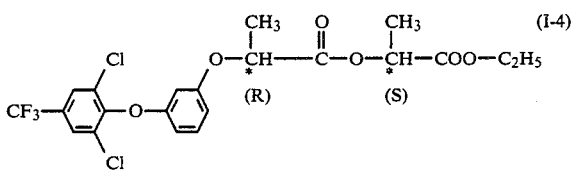

A mixture of 16.1 g (0.05 mol) of 2,6-dichloro-4-trifluoromethyl-3'-hydroxy-diphenyl ether, 8.2 g (0.06 mol) of potassium carbonate, 17.2 g (0.05 mol) of the tosylate of the formula

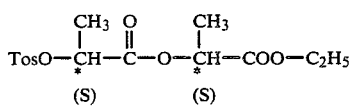

and 100 ml of acetonitrile were heated under reflux for 10 hours. Thereafter, the reaction mixture was cooled, and 200 ml of water were added. The resulting mixture was extracted with twice 100 ml of methylene chloride, and the combined organic phases were dried over sodium sulphate, and then evaporated down by stripping off the solvent under reduced pressure. The remaining residue was freed from residues of volatile constituents by gentle heating in a high vacuum. In this manner, 17 g (68% of theory) of the compound of the formula (I-4) were obtained.

$n_D^{20} = 1.5292$

Angle of rotation: $[\alpha]_D^{24} = -5.2°$ (1 molar solution in chloroform; cell length 10 cm).

EXAMPLE 5

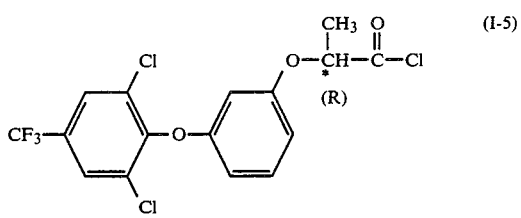

15 g (0.126 mol) of thionyl chloride were added dropwise to a stirred solution of 19.7 g (0.05 mol) of the R enantiomer of 2-[3-(2,6-dichloro-4-trifluoromethyl-phenoxy)-phenoxy]-propionic acid in 100 ml of toluene at 20° C. The mixture was heated to 100° C. for 2 hours. Thereafter, the reaction mixture was evaporated down by stripping off the volatile constituents under reduced pressure. In this manner, the R enantiomer of 2-[3-(2,6-dichloro-4-trifluoromethyl-phenoxy)-phenoxy]-propionic acid-chloride was obtained in the form of an oily product, which was used for the further reaction.

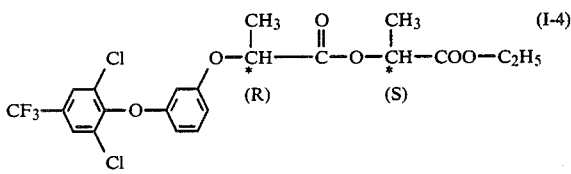

The R enantiomer of 2-[3-(2,6-dichloro-4-trifluoromethyl-phenoxy)-phenoxy]-propionic acid-chloride, prepared in the manner described above, was dissolved in 50 ml of toluene, and the solution was added dropwise to a mixture of 5.5 g (0.055 mol) of triethylamine and 11.8 g of the S enantiomer of ethyl lactate in 100 ml of toluene. Stirring was continued for 10 hours at 20° C., and the reaction mixture was then worked up by washing it with twice 100 ml of water and then evaporating it down by stripping off the solvent under reduced pressure. The remaining residue was freed from residues of volatile constituents by heating for a short time in a high vacuum. In this manner, 15 g (60% of theory) of the compound of the formula (I-4) were obtained.

Angle of rotation: $[\alpha]_D^{24} = -5.3°$ (1 molar solution in chloroform; cell length 10 cm).

Using the methods given in Examples 1 to 5, the substances listed in the examples below were also prepared.

EXAMPLE 6

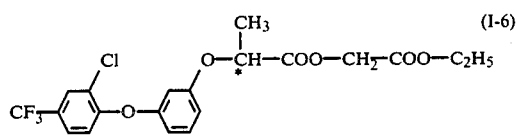
(I-6)

Yield: 77% of theory.
Angle of rotation: $[\alpha]_D^{24} = +6.72$.

EXAMPLE 7

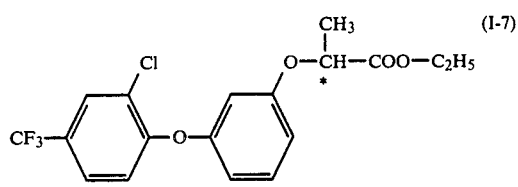
(I-7)

Yield: 54% of theory.
Refractive index: $n_D^{20} = 1.5171$.
Angle of rotation: $[\alpha]_D^{24} = +3.65°$.

EXAMPLE 8

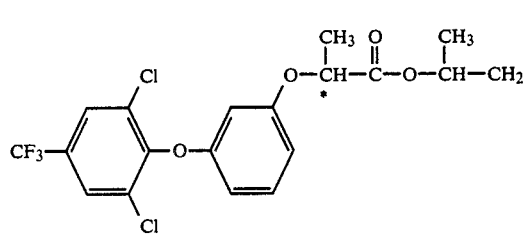
(I-8)

Yield: 67% of theory.
Angle of rotation: $[\alpha]_D^{24} = +0.16°$.

EXAMPLE 9

(I-9)

Cl—[benzene with CF3, Cl]—O—[benzene]—O—CH(CH3)—C(=O)—O—CH2—CH2—CH2—O—CH2—[phenyl]

Yield: 89% of theory.
Refractive index: $n_D^{20} = 1.5380$.
Angle of rotation: $[\alpha]_D^{24} = 0.89°$.

EXAMPLE 10

(I-10)

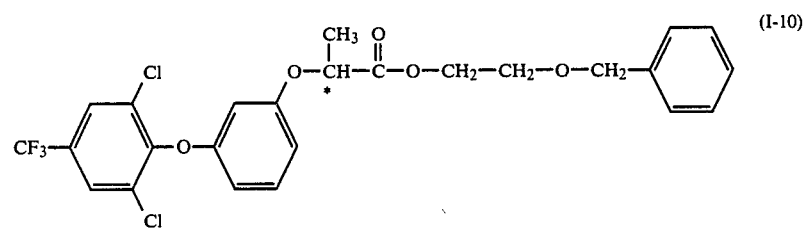

Yield: 65% of theory.
Refractive index: $n_D^{20} = 1.5415$

Angle of rotation: $[\alpha]_D^{24} = +1.1°$.

EXAMPLE 11

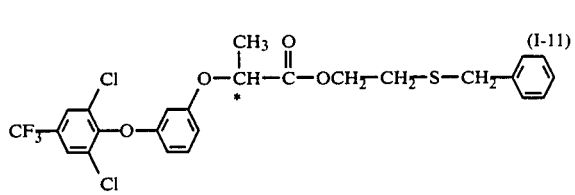
(I-11)

Yield: 77% of theory.
Refractive index: $n_D^{20} = 1.5554$.
Angle of rotation: $[\alpha]_D^{24} = +2.0°$.

EXAMPLE 12

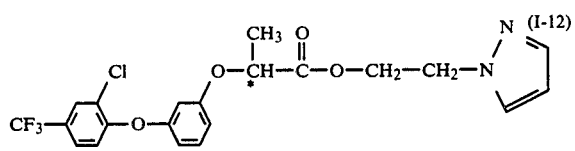
(I-12)

Yield: 45% of theory.
Refractive index: $n_D^{20} = 1.5065$.

Angle of rotation: $[\alpha]_D^{24} = 1.6°$.

EXAMPLE 13

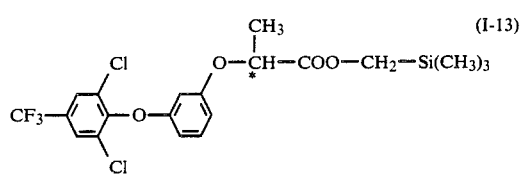
(I-13)

Yield: 68% of theory.
Angle of rotation: $[\alpha]_D^{24} = +4.3°$.

EXAMPLE 14

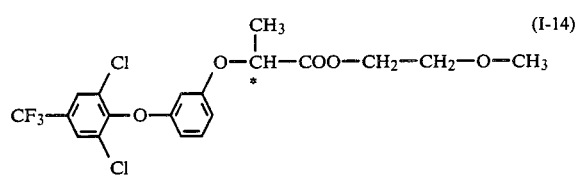
(I-14)

Yield: 65% of theory.
Angle of rotation: $[\alpha]_D^{24} = +1.7°$.

EXAMPLE 15

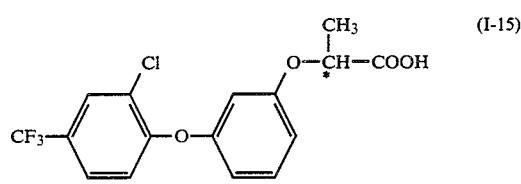
(I-15)

Yield: 86% of theory.
Angle of rotation: $[\alpha]_D^{24} = +1.52°$.

EXAMPLE 16

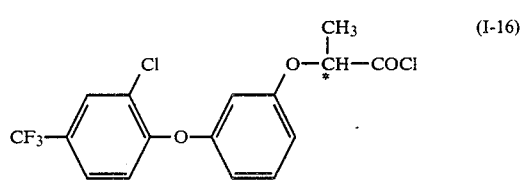
(I-16)

Yield: 90% of theory.
Refractive index: $n_D^{21} = 1.5298$
Angle of rotation: $[\alpha]_D^{24} = +0.37°$.

EXAMPLE 17

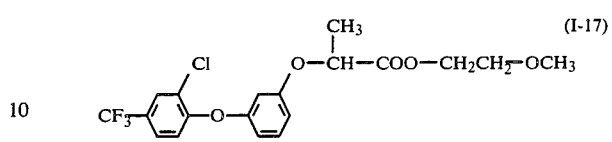
(I-17)

Yield: 74% of theory.
Angle of rotation: $[\alpha]_D^{24} = +3.45°$.

EXAMPLE 18

Preparation of the starting material of the formula:

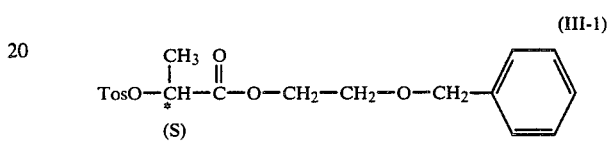
(III-1)

5.25 g (0.02 mol) of the S enantiomer of tosyloxylactoyl chloride were added to a stirred mixture of 3.32 g (0.02 mol) of glycol mono-benzyl ether, 2 g (0.02 mol) of triethylamine and 50 ml of toluene at 20° C. The mixture was stirred for a further 14 hours at 70° C., and the reaction mixture was then worked up by adding 100 ml of water, extracting the mixture several times with toluene, drying the combined organic phases and evaporating them down by stripping off the solvent under reduced pressure. In this manner, 6.3 g (80.5% of theory) of the S enantiomer of (2-benzyloxy)-ethyl 2-tosyloxy-propionate were obtained.

Angle of rotation: $[\alpha]_D^{24} = -10.2°$ (1 molar solution in chloroform; cell length 10 cm).

Using the method given in Example 18, the starting materials of the formula (III) which are listed as formulae in the table below were also prepared.

TABLE 1

$$Z-\overset{CH_3}{\underset{*}{C}H}-COO-R^5 \quad (III)$$
(S)

| Example No. | Compound | Z | R⁵ | Angle of rotation $[\alpha]_D^{24}$ |
|---|---|---|---|---|
| 19 | (III-2) | TosO | —CH₂—CH₂—O—CH₂—(2-F-phenyl) | −9.7° |
| 20 | (III-3) | TosO | —CH₂—CH₂—CH₂—O—CH₂—phenyl | −10.3° |

TABLE 1-continued $$\underset{(S)}{Z-\overset{CH_3}{\underset{|}{\overset{|}{C}H}}-COO-R^5} \quad (III)$$

| Example No. | Compound | Z | $R^5$ | Angle of rotation $[\alpha]_D^{24}$ |
|---|---|---|---|---|
| 21 | (III-4) | TosO | $-\overset{CH_3}{\underset{|}{C}H}-CH_2-O-CH_2-\text{C}_6\text{H}_5$ | $-4.1°$ |
| 22 | (III-5) | TosO | $-CH_2-CH_2-O-CH_2-\text{C}_6\text{H}_4-Cl$ | $-7.6°$ |
| 23 | (III-6) | TosO | $-CH_2-CH_2-S-CH_2-\text{C}_6\text{H}_5$ | $-10.9°$ |
| 24 | (III-7) | TosO | $-CH_2-CH_2-\text{N}(\text{imidazolyl})$ | $-11.4°$ |
| 25 | (III-8) | TosO | $-CH_2-\text{N}(\text{imidazolyl})$ | $-13.7°$ |
| 26 | (III-9) | TosO | $-\underset{(S)}{\overset{CH_3}{\underset{|}{\overset{|}{C}H}}}-COO-C_2H_5$ | $-17.8°$ |
| 27 | (III-10) | TosO | $-CH_2-COO-C_2H_5$ | $-11.6°$ |
| 28 | (III-11) | TosO | $-CH_2-Si(CH_3)_3$ | $-11.4°$ |

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
0% = no action (like untreated control)
100% = total destruction In this test, the active compounds according to the invention exhibit a very good herbicidal activity.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:
0% = no action (like untreated control)
100% = total destruction In this test, the active compounds according to Examples 7, 9, 10, 11 and 14 were very effective for combating Galium, Amaranthus and Portulaca in oats and wheat.

EXAMPLE C

Defoliation and desiccation of the leaves of cotton
Solvent: 30 parts by weight of dimethylformamide Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 1 week, the shedding of leaves and the desiccation of the leaves were rated, in comparison with the control plants, on the following scale:

0: denotes no desiccation of the leaves, no shedding of the leaves

+: denotes slight desiccation of the leaves, slight shedding of leaves

++: denotes severe desiccation of the leaves, severe shedding of leaves

+++: denotes very severe desiccation of the leaves, very severe shedding of leaves.

In this test, the compounds according to Examples 14, 15 and 17 exhibited a very strong activity.

What is claimed is:

1. An R enantiomer of phenoxypropionic acid compound of the formula

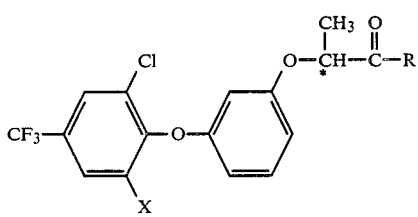

in which
X represents hydrogen or chlorine, and
R represents hydroxyl, alkoxy, with 1 to 4 carbon atoms, chlorine or the radical of the formula

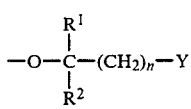

wherein
$R^1$ and $R^2$ independently of one another represent hydrogen or methyl,
n represents 0, 1 or 2 and
Y represents trimethylsilyl, pyrazolyl bonded via a ring nitrogen atom, or represents alkoxy with 1 to 4 carbon atoms, alkoxycarbonyl with 1 to 4 carbon atoms in the alkoxy part or the radical of the formula

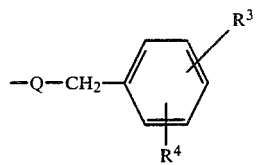

wherein
Q represents oxygen or sulphur and
$R^3$ and $R^4$ are hydrogen.

2. An R enantiomer according to claim 1 wherein X represents hydrogen.

3. An R enantiomer according to claim 1 wherein X represents chlorine.

4. An R enantiomer according to claim 1 wherein R represents hydroxyl.

5. An R enantiomer according to claim 1 wherein R represent alkoxy.

6. An R enantiomer according to claim 1 wherein R represents chlorine.

7. An R enantiomer according to claim 1 wherein R represents the radical

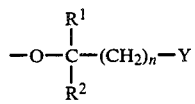

wherein $R^1$, $R^2$, Y and n have the meaning given in claim 1.

8. A compound according to claim 7 wherein Y represents the radical

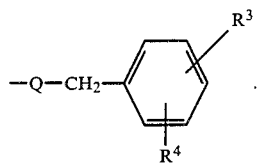

9. A compound according to claim 8 wherein Q is oxygen.

10. A compound according to claim 8 wherein Q is sulphur.

11. A compound according to claim 7 wherein $R^1$ and $R^2$ are hydrogen.

12. A compound according to claim 7 wherein n is 1.

13. A compound according to claim 7 wherein n is 2.

14. A compound according to claim 1 of the formula

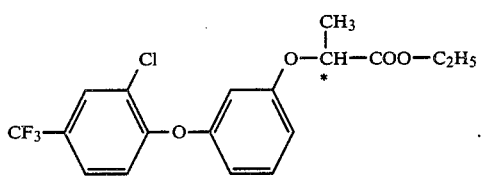

15. A compound according to claim 1 of the formula

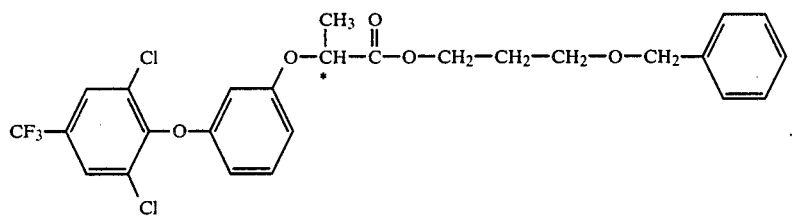

16. A compound according to claim 1 of the formula

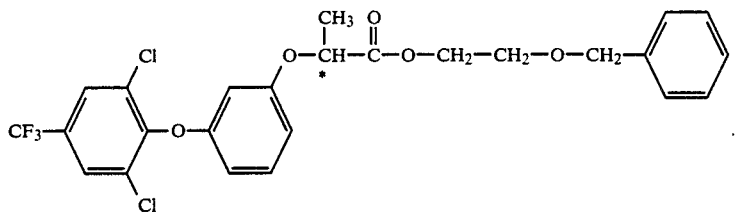

17. A compound according to claim 1 of the formula

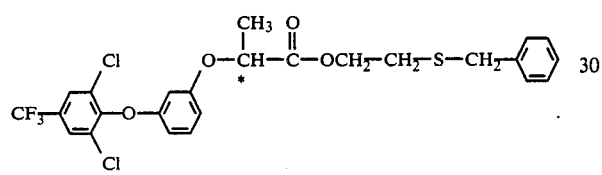

18. A compound according to claim 1 of the formula

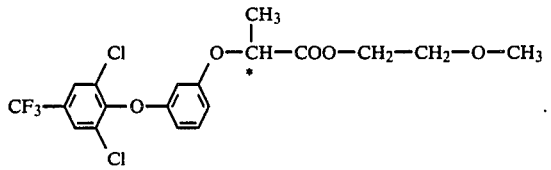

19. A herbicidal composition comprising an R enantiomer according to claim 1 in a herbicidally effective amount and a diluent.

20. A process for combating weeds which comprises applying to the weeds or their habitat a herbicidally effective amount of the R enantiomer of claim 1.